United States Patent [19]

Kantor

[11] Patent Number: 4,704,276

[45] Date of Patent: Nov. 3, 1987

[54] COMPOSITIONS AND METHODS FOR INCREASING THE GROWTH RATE OF MEAT PRODUCING ANIMALS, IMPROVING THE EFFICIENCY OF FEED UTILIZATION THEREBY AND ENHANCING LACTATION IN LACTATING RUMINANTS

[75] Inventor: Sidney Kantor, Cranbury, N.J.

[73] Assignee: American Cyanamid Company, Stamford, Conn.

[21] Appl. No.: 880,608

[22] Filed: Jun. 30, 1986

[51] Int. Cl.[4] .......................... A61K 35/74; C12P 1/06
[52] U.S. Cl. .................................... 424/122; 435/169
[58] Field of Search ......................................... 424/122

Primary Examiner—Jerome D. Goldberg
Attorney, Agent, or Firm—Alice C. Brennan

[57] ABSTRACT

This invention provides methods for increasing the growth rate of meat producing animals, for improving the efficiency of feed utilization by said meat producing animals, and for increasing lactation in lactating ruminant animals. The invention also relates to novel animal feed compositions and parenteral compositions useful in obtaining the above-described desired results.

22 Claims, 8 Drawing Figures

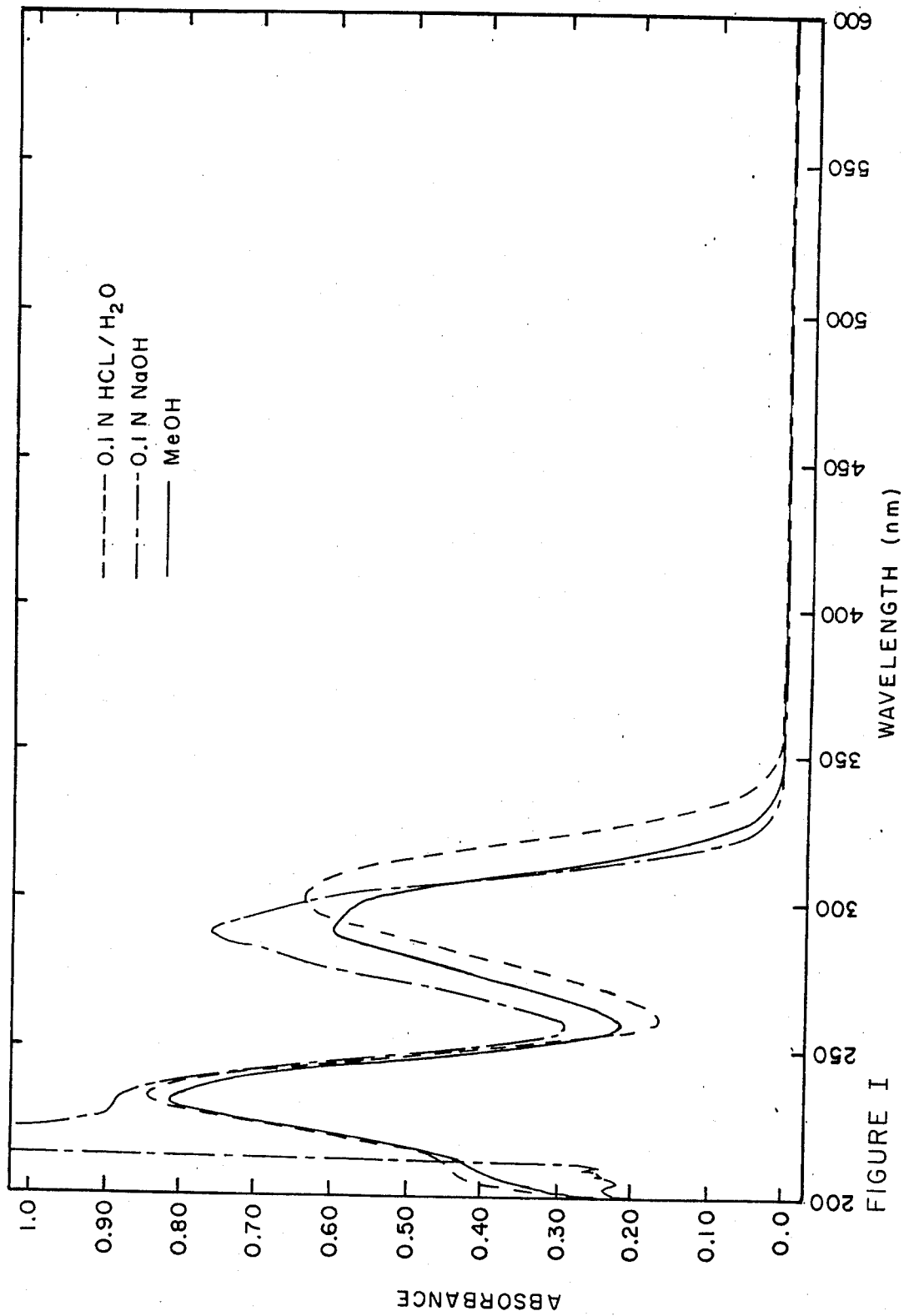

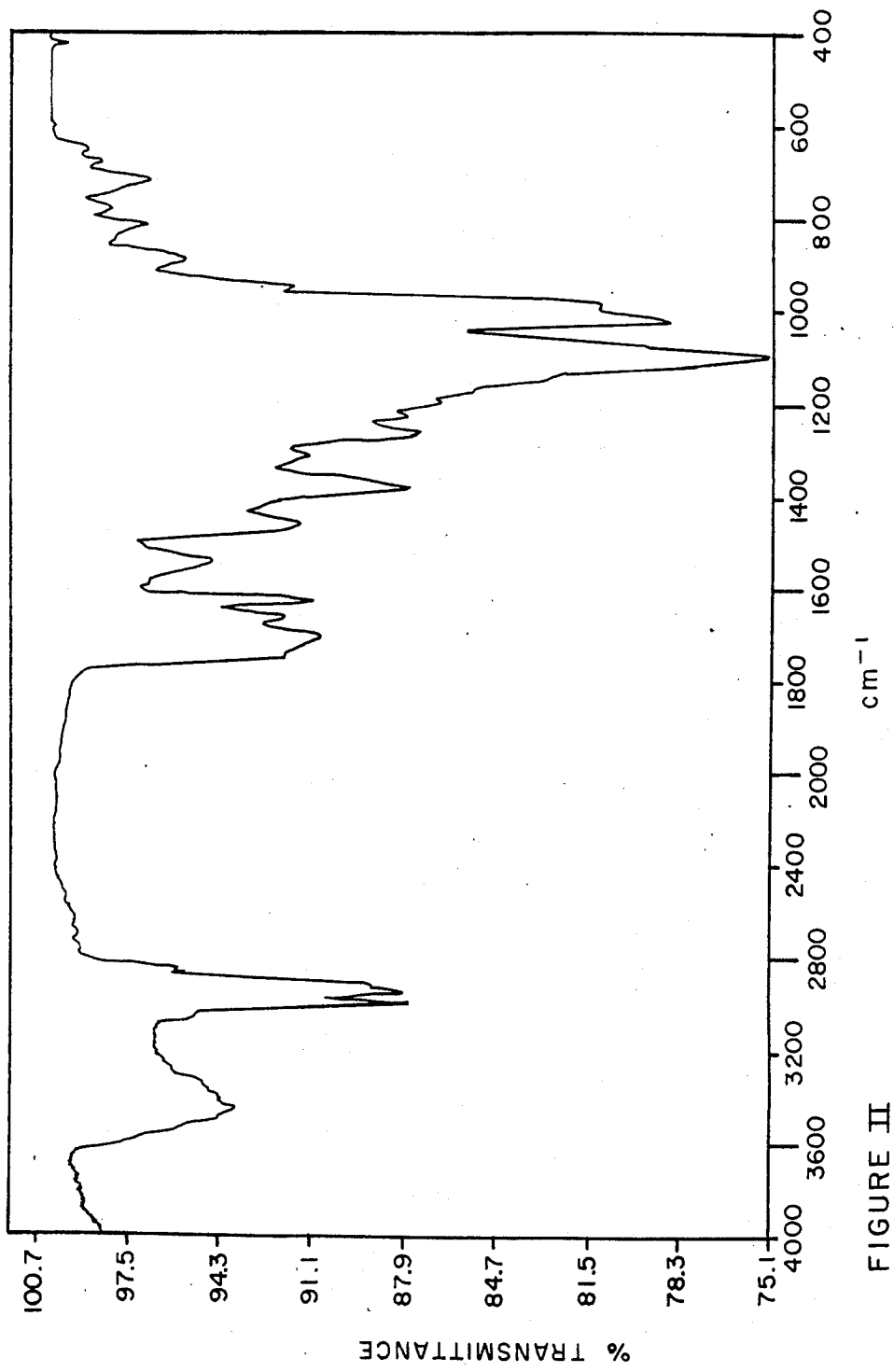
FIGURE II

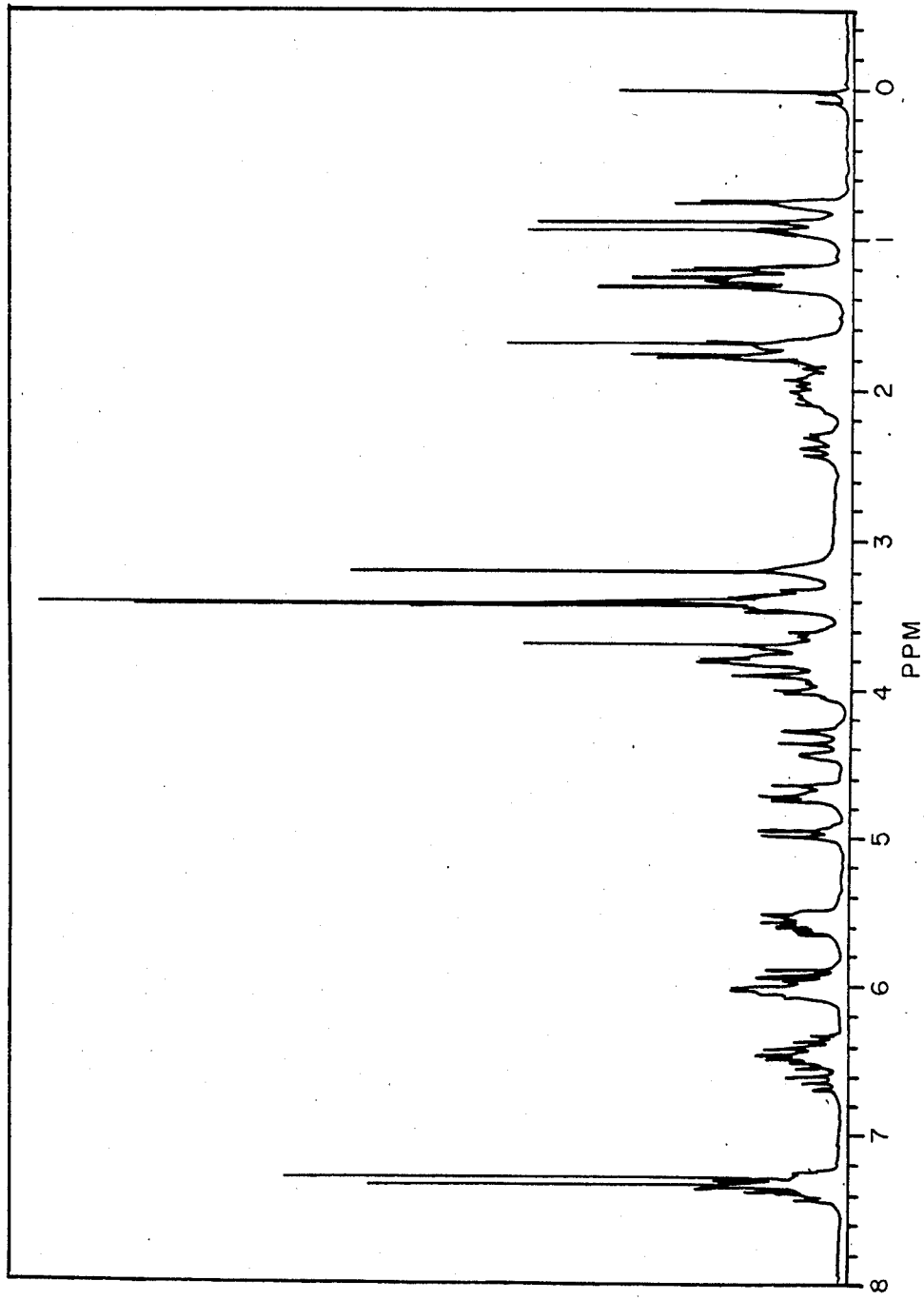
FIGURE III

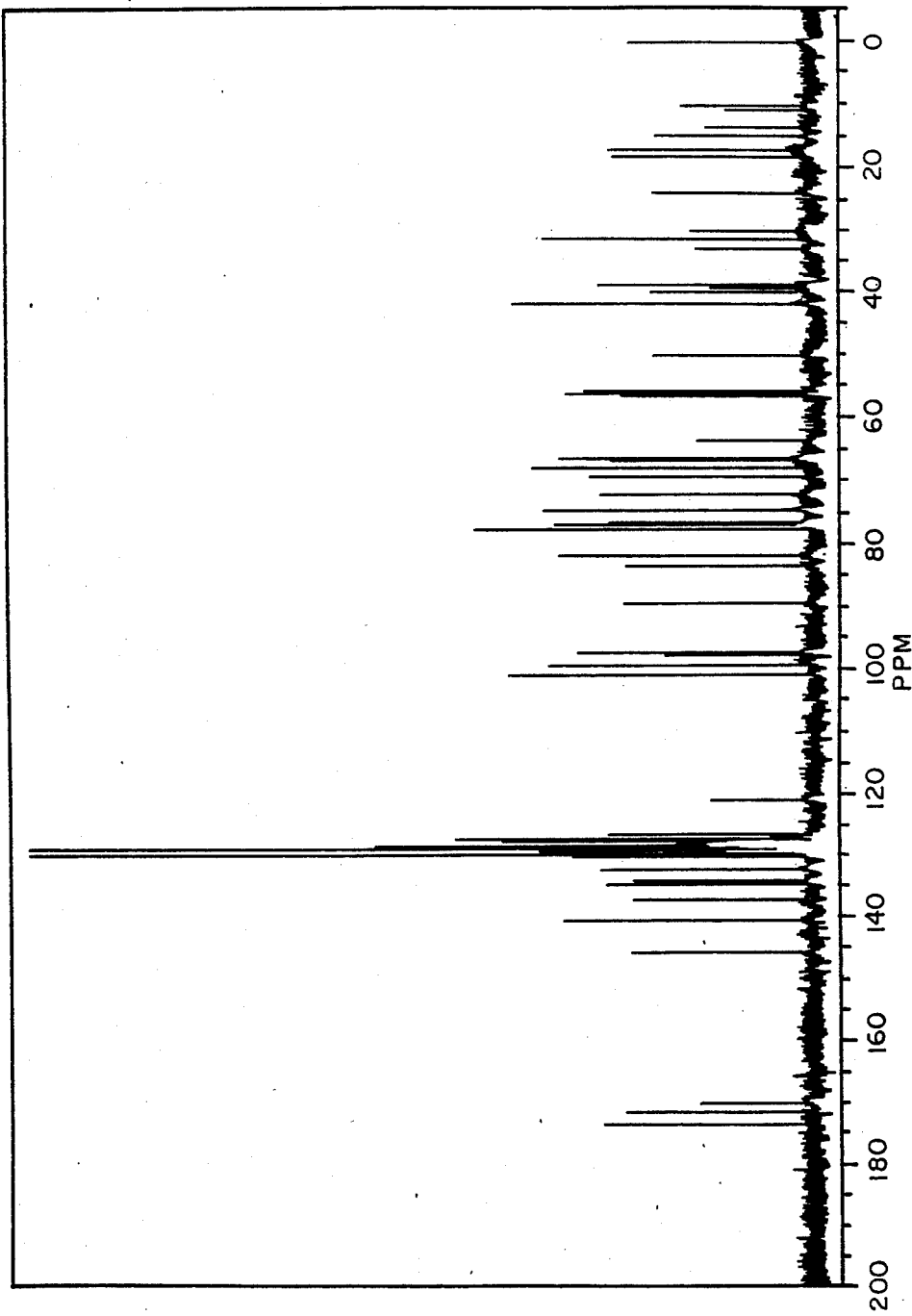

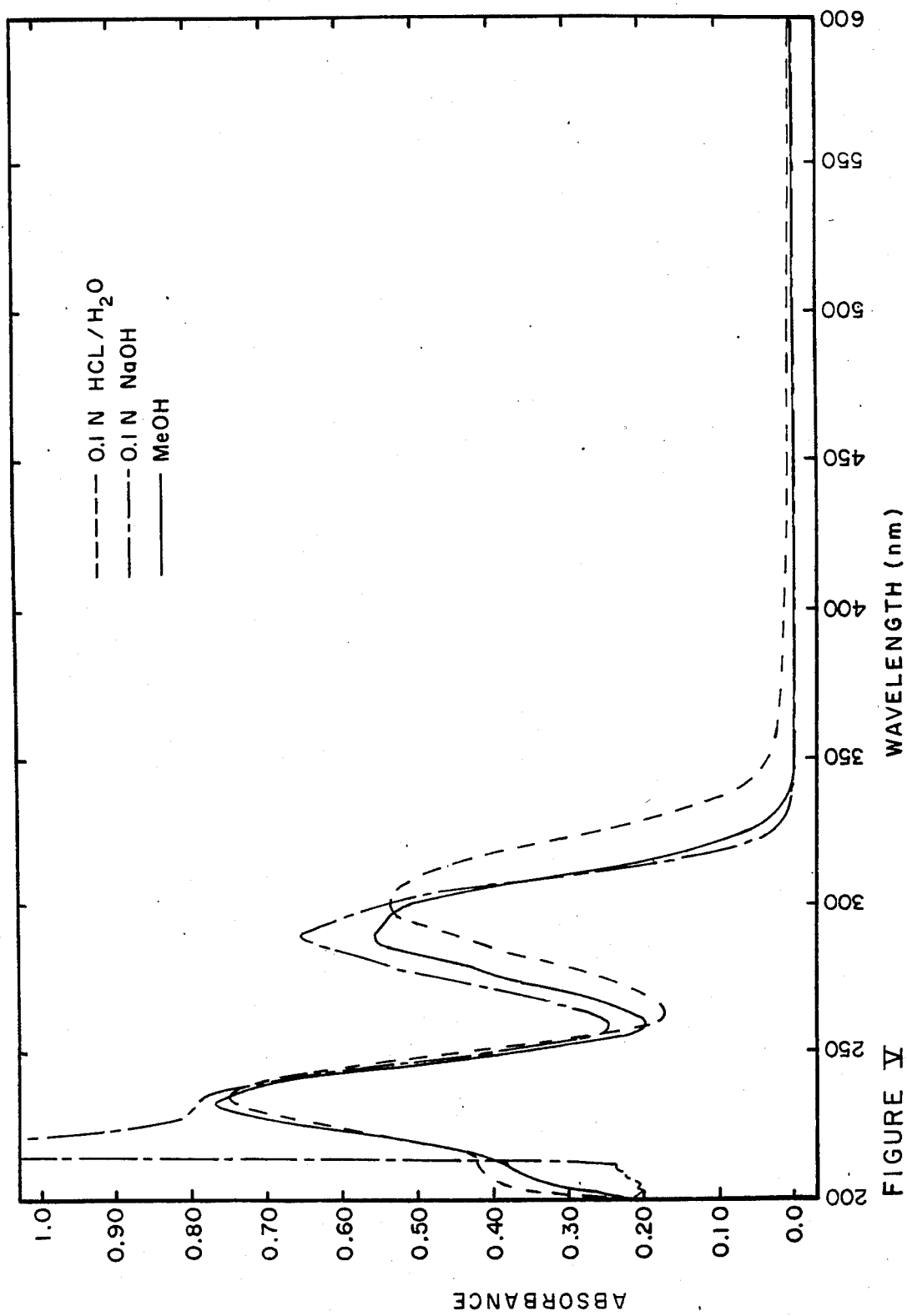

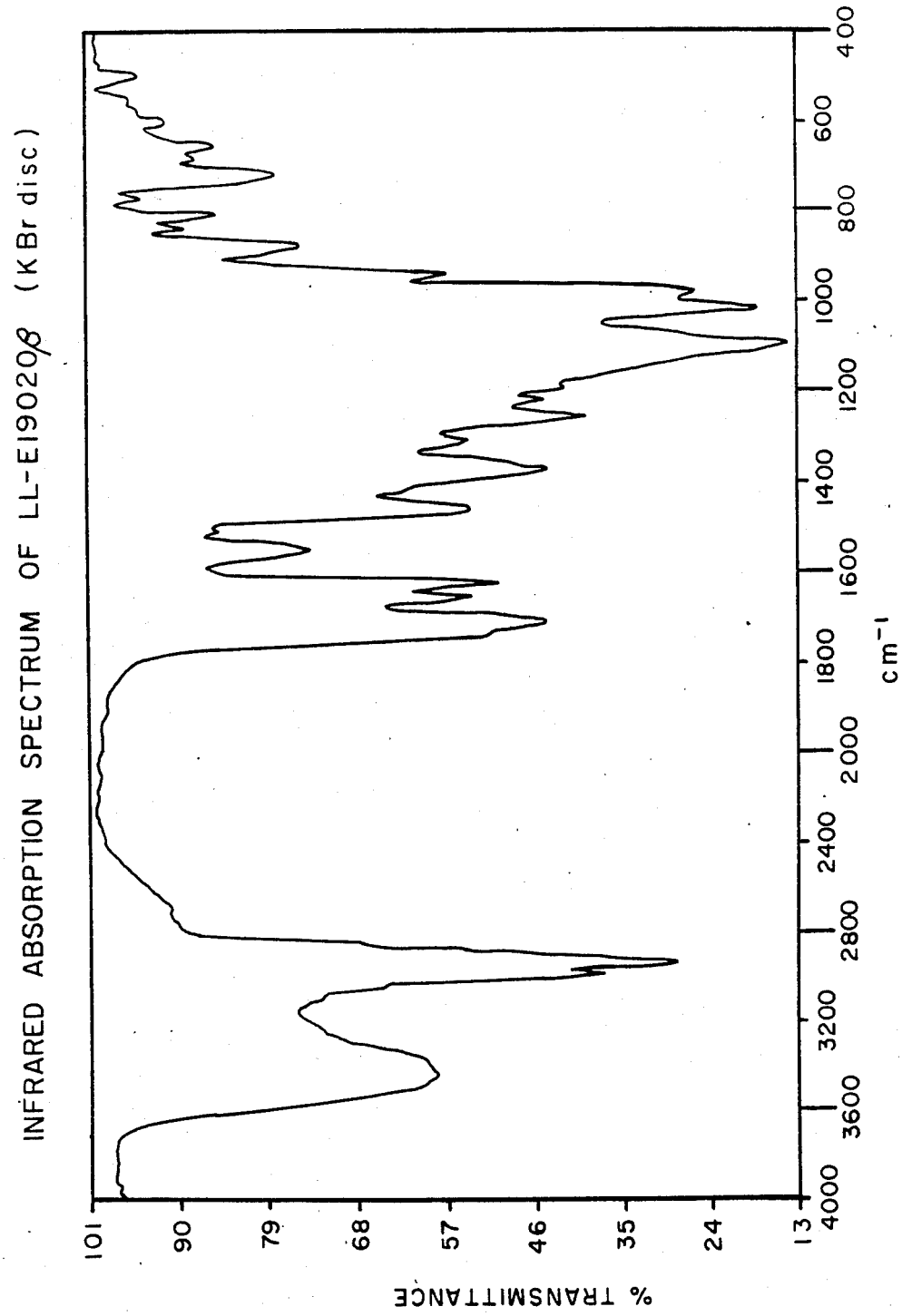
FIGURE VI

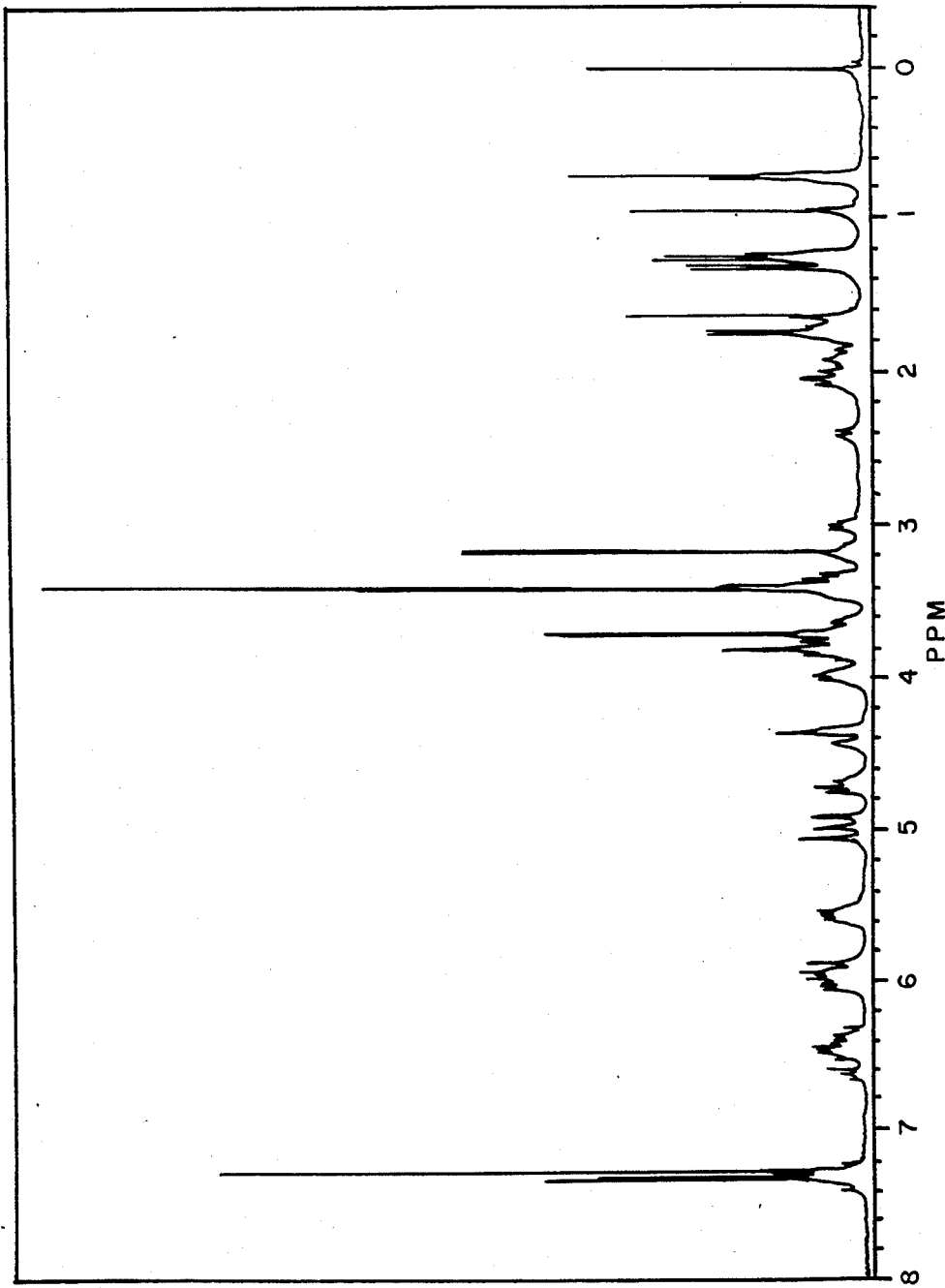

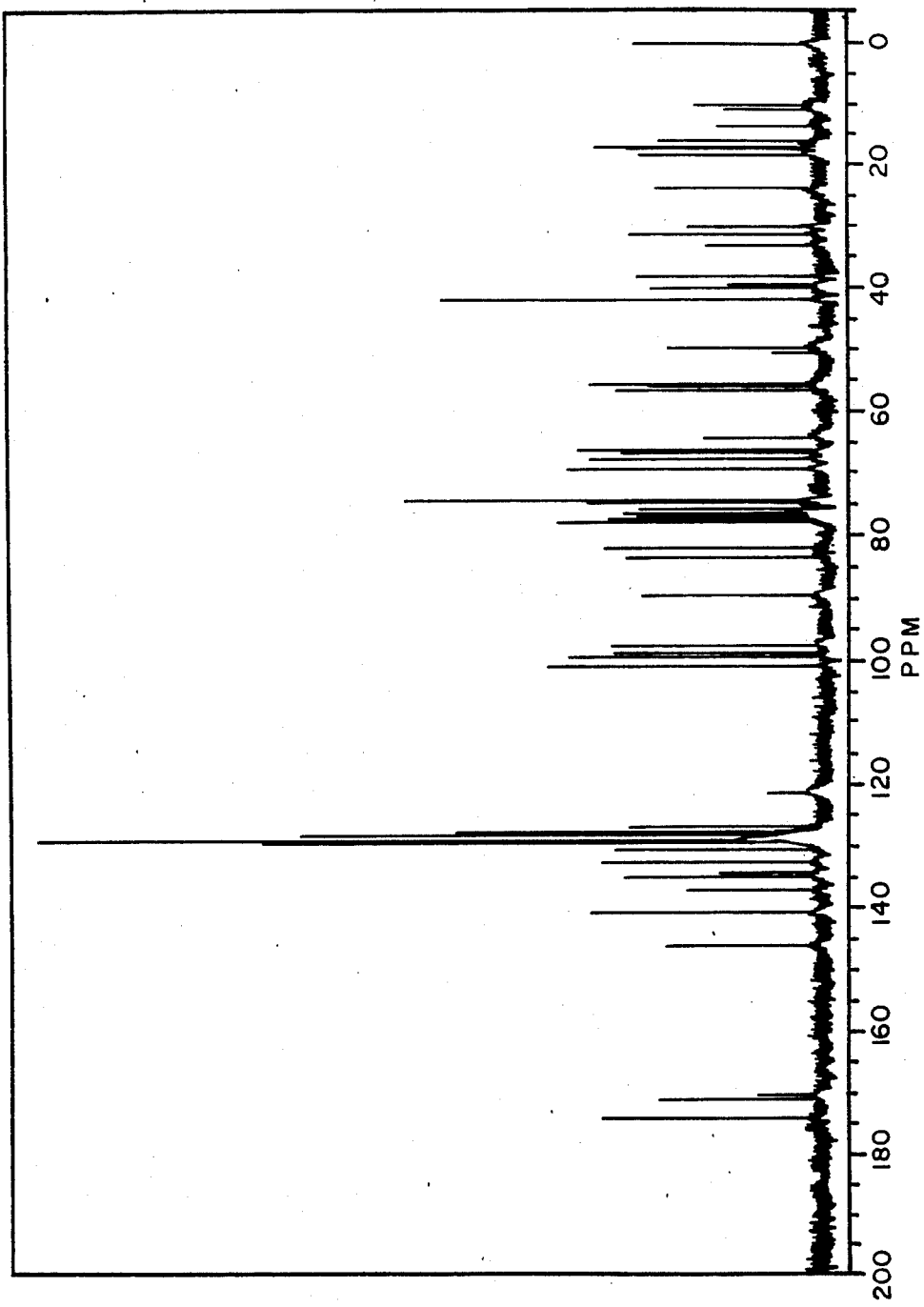
FIGURE VIII

COMPOSITIONS AND METHODS FOR INCREASING THE GROWTH RATE OF MEAT PRODUCING ANIMALS, IMPROVING THE EFFICIENCY OF FEED UTILIZATION THEREBY AND ENHANCING LACTATION IN LACTATING RUMINANTS

SUMMARY OF THE INVENTION

This invention relates to methods and compositions for increasing the growth rate of meat producing animals, improving the efficiency of feed utilization thereby and enhancing lactation in lactating ruminant animals. It also relates to animal feed compositions comprising an edible feed stuff and a sufficient amount of an antibiotic selected from LL-E19020α, LL-E19020β or a physiologically acceptable salt thereof, to increase the growth rate, improve the efficiency of feed utilization of meat producing animals and enhance lactation in lactating ruminants.

The antibiotics LL-E19020α and LL-E19020β and a method for their preparation are described in the application of G. T. Carter; M. Greenstein; J. J. Goodman; D. B. Borders; W. M. Maiese and R. T. Testa; field concurrently herewith and incorporated herein by reference thereto.

The compounds of this invention are useful for the treatment of both monogastric and ruminant animals. Moreover, said compounds are particularly effective for improving feed efficiency and inducing weight gains in cattle, sheep, swine, goats, rabbits, horses and poultry.

BRIEF DESCRIPTION OF THE DRAWINGS

FIG. I shows an ultraviolet absorption spectra of LL-E19020α.

FIG. II shows an infrared absorption spectrum of LL-E19020α.

FIG. III shows a proton nuclear magnetic resonance spectrum of LL-E19020α.

FIG. IV shows a carbon-13 nuclear magnetic resonance spectrum of LL-E19020α.

FIG. V shows an ultraviolet absorption spectra of LL-E19020β.

FIG. VI shows an infrared absorption spectrum of LL-E19020β.

FIG. VII shows a proton nuclear magnetic resonance spectrum of LL-E-19020β.

FIG. VIII shows a carbon-13 nuclear magnetic resonance spectrum of LL-E-19020β.

DESCRIPTION OF THE PREFERRED EMBODIMENTS

In accordance with the invention, the antibiotics LL-E19020α and LL-E19020β or salts thereof may be orally or parenterally administered to the animals. They may be administered in admixture with the animal's feed or as a top dressing therefore. They may also be proffered to said animals in the form of a bolus, pellet, tablet, pill, drench, oral gel or the like, or provided in the animal's drinking water.

When orally administered in or with the feed, generally about 0.1 to 300 grams of the antibiotic selected from LL-19020α, LL-E19020β or a physiologically acceptable salt thereof per ton of feed is effective for enhancing the growth rate and improving the efficiency of feed utilization by the host animals.

Although the requirements of feed utilization of lactating ruminants such as dairy cows differ measurably from those of ruminants raised for meat production, surprisingly the concentration of antibiotic in feed, as described above for meat producing animals, is also effective for increasing lactation in lactating ruminants.

Ruminal VFA production is particularly important, since it relates directly to the normal maintenance of the animal, as well as to the quality and quantity of the milk produced by the animal. In the lactating ruminant, however, energy for lactation is the most limiting factor in milk production. Acetate is required for milk fat synthesis, while propionate is utilized to produce glucose, which in turn is required for lactose synthesis, and also has a minor role in milk fat production. Butyrate is more glycogenic than lipogenic, the lipogenic aspect being indirect since butyrate must first be degraded to acetate units before it can be utilized for long chain fatty acid synthesis, i.e., milk fat.

Accordingly, in order to increase milk production in lactating ruminants, it is necessary to increase propionate production but not at a large expense of acetate and butyrate production. To this end it has now been established that oral administration of the abovesaid antibiotics to ruminants enhances the production of propionate in the rumen while simultaneously suppressing the production of acetate. As such, this treatment improves the propionate to acetate ratio in the animals rumen.

Since the antibiotics of the present invention are useful in the treatment of both monogastric and ruminant animals which may weigh only a few grams or as much as several thousand kilograms, the effective levels of antibiotic necessary for treating said animals will vary with the animals stage of development and from species to species. Effective levels for each animal species are therefore listed in Table 1 below:

TABLE 1

| Compound | Effective Antibiotic Levels For Different Animal Species | | | |
|---|---|---|---|---|
| | Effective Feed Level g/ton | mg/hd/day | mg/kg body wt | Animals |
| LL-E19020α or Salts Thereof | 0.1–300 | 0.1 mg–25 grams | 0.001–50 | Cattle & Horses |
| | 0.1–250 | 0.01 mg–2.5 grams | 0.01–50 | Sheep, Goats & Swine |
| | 0.1–200 | 0.001 mg–100 mg | 0.01–50 | Chickens, Turkeys and Rabbits |
| LL-E19020β or Salts Thereof | 0.1–300 | 0.1 mg–25 grams | 0.01–50 | Cattle & Horses |
| | 0.1–250 | 0.01 mg–2.5 grams | 0.01–50 | Sheep, Goats & Swine |
| | 0.1–200 | 0.001 mg–100 mg | 0.01–50 | Chickens, Turkeys and Rabbits |

Animal feed compositions which will provide the desired growth promotion and feed efficiency in the above-mentioned animals can be prepared by admixing the above said antibiotic or salt thereof, or an animal feed supplement containing said compound, with a sufficient quantity of an appropriate animal feed to provide the desired level of active compound in said feed.

Animal feed supplements can be prepared by admixing about 1.0% to 75% by weight of the antibiotic or salt thereof, with about 99% to 25% by weight of carriers or diluents. Carriers or diluents suitable for use in the preparation of the feed supplements include the following: alfalfa meal, soybean meal, cottonseed oil meal, linseed oil meal, sodium chloride, corn meal, cane molasses, urea, bone meal, fish meal, corncob meal, calcium chloride, and other similar materials. Use of the carriers or diluents in feed supplements promote uniformity of distribution of the active ingredient in the finished feed into which the supplement is blended. It thus performs an important function by ensuring proper distribution of the active ingredient throughout the feed.

If the supplement is used as a top dressing for feed, it helps to ensure uniformity of distribution of the active material across the top of the dressed feed.

For parenteral administration, the antibiotic or antibiotic salt may be prepared in the form of a paste or pellet and administered as an implant, usually under the skin of the head or ear of the animal in which enhanced growth rate and/or improved efficiency of feed utilization is desired.

In practice, parenteral administration generally involves injection of a sufficient amount of the above said antibiotic or antibiotic salt to provide the animal with from about 0.0001 to 50 mg/kg of body weight of the active ingredient.

Paste formulations can be prepared by dispersing the antibiotic or antibiotic salt in a pharmaceutically acceptable oil, such as, for example, peanut oil, sesame oil and corn oil.

Pellets containing an effective level of the antibiotic LL-E19020α or LL-E19020β can be prepared by admixing the above-said antibiotic with a diluent, such as carbowax, biodegradable polymers, carnauba wax, or the like. A lubricant, such as, magnesium stearate or calcium stearate may be added to improve the pelleting process if desired.

It is, of course, recognized that more than one pellet may be administered to an animal to achieve the desired dose level which will provide the increased growth rate and/or improve efficiency of feed utilization by said animal. Moreover, it has been found that additional implants may also be introduced periodically during the treatment period in order to maintain the proper drug release rate in the animal's body.

The antibiotics of this invention, LL-E19020α and LL-E19020β, are formed during the cultivation under controlled conditions of a new strain of *Streptomyces lydicus* ssp. *tanzanius*.

This microorganism is maintained in the culture collection of the Medical Research Division, American Cyanamid Company, Pearl River, NY as culture number LL-E19020. A viable culture of this new microorganism has been deposited with the Patent Culture Collection Laboratory, Northern Regional Research Center, U.S. Department of Agriculture, Peoria, Ill. 61604, and has been added to its permanent collection. It has been assigned the strain designation NRRL 18036 by said depository. Access to said culture, under strain designation NRRL 18036, during pendency of the instant application shall be available to one determined by the Commissioner of Patents and Trademarks to be entitled thereto under 37 C.F.R. §1.14 and 35 U.S.C. §122, and all restrictions on availability to the public of such culture will be irrevocably removed upon grant of a patent on the instant application.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus Streptomyces.

In the ISP tests for utilization of carbohydrates, LL-E19020 shows growth on arabinose, fructose, inositol, mannitol, raffinose, rhamnose, sucrose and xylose. Cellulose is not utilized.

The reactions of LL-E19020 in the Gordon physiological series are compared in Table 2 with those of *Streptomyces lydicus* ISP 5461 which it most closely resembles morphologically and physiologically. Because LL-E19020 differs from ISP 5461 in five characteristics (xanthine hydrolysis, decarboxylation of oxalate, acid from erythritol, rhamnose and β-methyl-D-xyloside) it is designated as a subspecies of *Streptomyces lydicus*.

TABLE 2

| Gordon Test Reactions of LL-E19020 and *Streptomyces lydicus* ISP 5461 | | |
|---|---|---|
| Reaction | LL-E19020 | ISP 5461 |
| Degradation/Transformation of | | |
| Casein | + | + |
| Xanthine | − | + |
| Hypoxanthine | + | + |
| Tyrosine | + | + |
| Adenine | + | + |
| Production of | | |
| Amylase | + | + |
| Gelatinase | + | + |
| Phosphatase | + | + |
| Nitrate Reductase | − | − |
| Urease | + | + |
| Esculinase | + | + |
| Growth on/in | | |
| 5% Sodium chloride | + | + |
| Salicylate | − | − |
| Lysozyme Broth | trace | trace |
| Utilization | | |
| Acetate | + | + |
| Benzoate | − | − |
| Citrate | + | + |
| Lactate | + | + |
| Malate | + | + |
| Mucate | + | + |
| Oxalate | + | − |
| Propionate | + | + |
| Pyruvate | + | + |
| Succinate | + | + |
| Tartrate | − | − |
| Growth at | | |
| 10° C. | + | + |
| 42° C. | − | − |
| 50° C. | − | − |
| Acid from | | |
| Adonitol | + | + |
| Arabinose | + | + |
| Cellobiose | + | + |
| Dextrin | + | + |
| Dulcitol | − | − |
| Erythritol | + | − |
| Fructose | + | + |
| Galactose | + | + |
| Glucose | + | + |
| Glycerol | + | + |
| Inositol | + | + |
| Lactose | + | + |
| Maltose | + | + |
| Mannitol | + | + |

TABLE 2-continued
Gordon Test Reactions of LL-E19020
and *Streptomyces lydicus* ISP 5461

| Reaction | LL-E19020 | ISP 5461 |
|---|---|---|
| Mannose | + | + |
| Melibiose | + | + |
| α-Methyl-D-Glucoside | + | + |
| Raffinose | + | + |
| Rhamnose | + | − |
| Salicin | + | + |
| Sorbitol | + | + |
| Sucrose | + | + |
| Trehalose | + | + |
| Xylose | + | + |
| β-Methyl-D-Xyloside | + | − |

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure to X-radiation, ultraviolet radiation, N'-nitro-N-nitrosoguanidine, actinophages and the like.

GENERAL FERMENTATION CONDITIONS

Cultivation of *Streptomyces lydicus* ssp. *tanzanius* NRRL 18036 may be carried out in a wide variety of liquid culture media. Media which are useful for the production of LL-E19020α and LL-E19020β include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

GENERAL PROCEDURE FOR THE ISOLATION OF LL-E19020α and LL-E19020β

The LL-E19020α and LL-E19020β antibiotics are recovered from the fermentation broth by pH adjustment to 4.5–5.5, filtration through diatomaceous earth, extraction into a solvent such as ethyl acetate, concentration, dissolution in a solvent such as dichloromethane and purification by column chromatography on silica gel using successively, dichloromethane and methanol:-dichloromethane (1:4), giving a crude product.

The crude product is then separated into the α and β components and further purified by high performance liquid chromatography on a reverse-phase column using the system acetonitrile, 0.1M ammonium acetate buffer pH 4.3 (1:1).

The physico-chemical characteristics of LL-E19020α are as follows:

LL-E19020α

1. Approximate elemental analysis: C 62.73; H 7.60; N 1.00; O 28.67 (by difference);
2. Molecular weight: 1225 (FABMS);
3. Apparent molecular formula: $C_{64}H_{91}NO_{22}$;
4. Specific rotation: $[\alpha]_D^{26} = 0$ (C 0.385, methanol);
5. Ultraviolet absorption spectra: as shown in FIG. I $UV_{MAX}^{CH3OH} = 233$ nm (ε 49,800); 290 nm (ε 36,600).
6. Infrared absorption spectrum: as shown in FIG. II (KBr disc): 3420, 2970, 2925, 1717, 1695, 1647, 1617, 1525, 1445, 1365, 1092, 1018 cm$^{-1}$;
7. Proton nuclear magnetic resonance spectrum: as shown in FIG. III (300 MHz, CDCl$_3$);
8. Carbon-13 nuclear magnetic resonance spectrum: as shown in FIG. IV (75 MHz, CDCl$_3$, ppm downfield from TMS), significant peaks as listed below:

| | | | | | |
|---|---|---|---|---|---|
| 173.3 | 129.0 | 97.3 | 74.2 | 55.4 | 17.2 |
| 171.4 | 128.6(2×) | 97.0 | 72.0 | 49.8 | 17.0 |
| 170.1 | 128.43 | 89.2 | 71.9 | 41.8 | 14.8 |
| 145.7 | 128.38 | 83.3 | 69.1 | 39.8 | 13.5 |
| 140.3 | 128.1(2×) | 81.6 | 67.5 | 39.1 | 10.8 |
| 137.0 | 127.5 | 77.6 | 66.4 | 38.8 | 10.0 |
| 134.4 | 127.1 | 77.0 | 66.1 | 32.9 | |
| 133.9 | 126.3 | 76.4 | 63.5 | 31.0 | |
| 132.0 | 120.8 | 74.6 | 56.5 | 29.9 | |
| 130.1 | 100.6 | 74.5 | 56.0 | 23.8 | |
| 129.5(2×) | 99.0 | 74.4 | 55.6 | 18.1 | |

2× = two overlapping signals

LL-E19020β

1. Approximate elemental analysis: C 63.33; H 7.72; N 1.16; O 27.79 (by difference);
2. Molecular weight: 1225 (FABMS);
3. Apparent molecular formula: $C_{64}H_{91}NO_{22}$;
4. Specific rotation: $[\alpha]_D^{26} = -17 \pm 2$ (C 0.455, methanol);
5. Ultraviolet absorption spectra: as shown in FIG. V $UV_{MAX}^{CH3OH} = 233$ nm (ε 47,000); 290 nm (ε 34,100). $UV_{MAX}^{0.1N\ HCl} = 234$ nm (ε 46,000); 301 nm (ε 32,800).
$UV_{MAX}^{0.1N\ NaOH} = 217$ nm (ε 77,800); 290 nm (ε 39,700).
6. Infrared absorption spectrum: as shown in FIG. VI (KBr disc): 3430, 2970, 2930, 1712, 1648, 1620, 1543, 1454, 1367, 1265, 1098, 1020, 980 cm$^{-1}$;
7. Proton nuclear magnetic resonance spectrum: as shown in FIG. VII (300 MHZ, CDCl$_3$);
8. Carbon-13 nuclear magnetic resonance spectrum, as shown in FIG. VIII (75 MHz, CDCl$_3$, ppm downfield TMS), significant peaks as listed below:

| | | |
|---|---|---|
| 173.6 | 99.0 | 55.4 |
| 170.6 | 98.4 | 49.6 |
| 170.0 | 97.2 | 41.6(2×) |
| 145.6 | 89.2 | 39.8 |
| 140.2 | 83.3 | 39.1 |
| 136.7 | 81.6 | 38.0 |
| 134.4 | 77.6 | 32.9 |
| 133.9 | 77.5 | 31.1 |
| 132.0 | 76.2 | 29.9 |
| 130.1 | 75.5 | 23.7 |
| 129.1(2×) | 74.6 | 18.1 |
| 128.9 | 74.5 | 17.2 |
| 128.6(2×) | 74.2 | 17.0 |
| 128.5 | 69.1 | 16.2 |
| 128.4 | 68.9 | 13.5 |
| 128.3 | 67.5 | 10.8 |
| 128.2 | 66.6 | 10.0 |
| 127.8 | 66.1 | |
| 127.2 | 64.1 | |
| 126.5 | 56.5 | |
| 120.9 | 56.0 | |
| 100.6 | 55.6 | |

2× = two overlapping signals

EXAMPLE 1

Evaluation of test compounds for increasing the growth of chickens and improving the efficiency of feed utilization thereby In this test one day old Peterson X Arbor Acres chicks are sorted into equal weight groups of 5 males and 5 females per cage. Cages are randomized to treatment groups with six replicates per treatment. Each compound is tested at 50 and 100 ppm in the diet and evaluated against chicks receiving a non-medicated diet.

The chicks are weighed at the start of the test and at 1 week intervals thereafter to the conclusion of said test. The chicks are given free access to feed and water during the entire test period. The feed is weighed when provided to the chicks and excess feed collected and weighed when the cages are cleaned.

The poultry diet employed in the test is as follows:
Vitamin-amino acid premix: 0.5%
Trace minerals: 0.1%
Sodium chloride: 0.3%
Dicalcium phosphate: 1.2%
Ground limestone: 0.5%
Stabilized fat: 4.0%
Dehydrated alfalfa, 17% protein: 2.0%
Corn gluten meal, 41% protein: 5.0%
Menhaden fish meal, 60% protein: 5.0%
Soybean oil meal, 44% protein: 30.0%
Ground yellow corn, fine to: 100.0%

The vitamin-amino acid premix in the above feed composition is prepared from the following formulation. The expressions of quantity relate to units per kilogram of the finished feed composition.
Butylated hydroxy toluene: 125.0 mg
dl-Methionine: 500.0 mg
Vitamin A: 3300.0 I.U.
Vitamin $D_3$: 1100.0 I.C.U.
Riboflavin: 4.4 mg
Vitamin E: 2.2 I.U.
Niacin: 27.5 mg
Panthothenic acid: 8.8 mg
Choline chloride: 500.0 mg
Folic acid: 1.43 mg
Menadione sodium bisulfate: 1.1 mg
Vitamin $B_{12}$: 11.0 mcg
Ground yellow corn, fine to: 5.0 mg Data obtained are reported in Table 3 below where it can be seen that antibiotics LL-E19020α and LL-E19020β both improved the weight gains of chicks and increased the efficiency of feed utilization thereby over unmedicated controls.

TABLE 3

Evaluation of Test Compounds For Increasing The Growth Rate of Poultry And Improving the Efficiency of Feed Utilization Thereby.

| Treatment | ppm | Weight Gains % Improvement over Controls | | | Feed/Gain | | |
|---|---|---|---|---|---|---|---|
| | | 0-1 Wk | 0-2 Wk | 0-3 Wk | 0-1 Wk | 0-2 Wk | 0-3 Wk |
| Control | — | — | — | — | 1.21 | 1.33 | 1.43 |
| Antibiotic (E 19020 alpha) | 50 | 12.5** | 4.1* | 4.2* | 1.11* | 1.30 | 1.38 |
| | 100 | 8.9* | 6.3** | 6.1** | 1.12* | 1.27 | 1.39 |
| Antibiotic (E 19020 beta) | 50 | 12.7** | 4.5* | 5.3* | 1.11* | 1.31 | 1.40 |
| | 100 | 10.7* | 5.1* | 5.9** | 1.13* | 1.29 | 1.38 |

*p = .05
**p = .01

EXAMPLE 2

Evaluation of test compounds for increasing the weight gain of poultry and improving the efficiency of feed utilization thereby Five male and five female one day old Peterson X Arbor Acres chicks are allotted to starter battery cages by weight. Cages are randomized to treatment groups with seven replicates per treatment. Each compound is tested at 12.5, 25, 50, 100 and 200 ppm in the diet. The positive standard is penicillin at 200 ppm. Diets are prepared weekly. This study has unusually high mortality (6.2%). Mortality is usually less than 3%. The high mortality is apparently due to toe clipping the males for identification since male deaths outnumbered female deaths by 3:1 ratio. In addition male weight gain improvements were lower than female weight gain improvements, which is not the case in the first study. The data is summarized in Tables 4 and 4A.

The diet employed in this test is the same as described in Example 1 above.

TABLE 4

Weight Gain And Feed Efficiency Of Broiler Chicks Treated With Antibiotics LL-E19020 Alpha And LL-E19020 Beta

| TREATMENT | PPM | Wg Gains And Feed Efficiency % Improvement Over Controls | | | FEED/GAIN |
|---|---|---|---|---|---|
| | | FEMALES | MALES | COMBINED | |
| Control | 0 | — | — | — | 1.41 |
| Penicillin | 200 | 4.2 | 2.4 | 3.5 | 1.35** |
| E19020 alpha | 12.5 | 7.8* | 0 | 3.8 | 1.36* |
| E19020 alpha | 25 | 4.8 | 5.9 | 5.5 | 1.34** |
| E19020 alpha | 50 | 10.5** | 3.6 | 6.6* | 1.34** |
| E19020 alpha | 100 | 3.2 | 2.9 | 2.9 | 1.34** |
| E19020 alpha | 200 | 7.1 | 4.5 | 5.7 | 1.32** |
| E19020 beta | 12.5 | 6.0 | 0 | 2.6 | 1.33** |
| E19020 beta | 25 | 5.1 | 2.4 | 3.4 | 1.38* |
| E19020 beta | 50 | 4.6 | 0 | 2.2 | 1.38* |
| E19020 beta | 100 | 7.2 | 1.7 | 4.5 | 1.34** |
| E19020 beta | 200 | 1.4 | 4.2 | 2.7 | 1.35** |

*probability (p) = 0.05
**probability (p) = 0.01

Following the above procedure but altering the rates of administration, and extending the test period to 7 weeks, feed efficiency and weight gains of chicks was again determined and data obtained are reported in Table 4 below.

TABLE 4A

| WEIGHT GAINS IN BROILER CHICKS TREATED WITH E19020 ALPHA | | | |
|---|---|---|---|
| 0-3 WEEKS | | 0-7 WEEKS | |
| WEIGHT GAIN | % IMPROVEMENT | WEIGHT GAIN | % IMPROVEMENT |

TABLE 4A-continued

| | PPM | IN GRAMS | OVER CONTROLS | IN GRAMS | OVER CONTROLS |
|---|---|---|---|---|---|
| Control | 0 | 608 | — | 2145 | — |
| Penicillin | 200 | 638* | 4.9 | 2217 | 3.4 |
| E19020 alpha | 6.25 | 635* | 4.4 | 2183 | 1.8 |
| | 12.5 | 647* | 6.3 | 2198 | 2.5 |
| | 25 | 659** | 8.4 | 2267* | 5.7 |
| | 50 | 642* | 5.6 | 2206 | 2.8 |
| | 100 | 652** | 7.3 | 2204 | 2.8 |

| FEED EFFICIENCY IN BROILER CHICKS TREATED WITH E19020 ALPHA | | | | | |
|---|---|---|---|---|---|
| | | 0–3 WEEKS | | 0–7 WEEKS | |
| | PPM | FEED/GAIN | % IMPROVEMENT OVER CONTROLS | FEED/GAIN | % IMPROVEMENT OVER CONTROLS |
| Control | 0 | 1.43 | — | 1.99 | — |
| Penicillin | 200 | 1.38** | 3.5 | 1.87** | 6.0 |
| E19020 alpha | 6.25 | 1.38** | 3.5 | 1.89** | 5.0 |
| | 12.5 | 1.38** | 3.5 | 1.91** | 4.0 |
| | 25 | 1.38** | 3.5 | 1.89** | 5.0 |
| | 50 | 1.39* | 2.8 | 1.91** | 4.0 |
| | 100 | 1.35** | 5.6 | 1.91** | 4.0 |

*$p < .05$
**$p < .01$
E19020 alpha lot #6951C-86A

EXAMPLE 3

Determination of Propionate Enhancement Activity By Oral Administration Of Test Compounds In these tests strained rumen fluid (2.5 ml) obtained from a fistulated steer is incubated anaerobically at 39° C. with 2.5 ml of McDougall's artificial saliva buffer containing 12.5 mg/ml of substrate (60.5% corn starch, 25.9% essential amino acid mixture and 13.6% alpha-cellulose) and appropriate concentrations of drug for 20–24 hr in a shaking water bath using sealed vials with gas release valves. The drugs are dissolved or suspended (sonified if necessary) in a 0.1% Tween 20-ethanol-water vehicle and 25–50 ul is added to the incubation. The reaction is terminated with 6N HCl and centrifuged at 20.000×g. Aliquots of the supernatant are analyzed for volatile fatty acid (VFA) content by gas-liquid chromatography.

Compounds causing an enhancement of propionate production determined by a decrease in the acetate/propionate ratio in this test have generally been found to increase feed efficiency in ruminants. The data is summarized in Tables 5 and 6.

TABLE 5

Propionate Enhancement Activity Of Test Compounds During In Vitro Rumen Fermentation

| TREATMENT[a] (PPM) | TOTAL VFA (mM) | (S.D.) | A:P | % DECREASE FROM CONTROL A:P |
|---|---|---|---|---|
| Control[b] | 159.4 | 4.2 | 2.65 | — |
| Antibiotic LL-E19020α | | | | |
| 0.008 | 161.2 | 0.2 | 2.66 | 0.0 |
| 0.031 | 158.4 | 5.4 | 2.43 | 8.4 |
| 0.125 | 159.2 | 1.8 | 2.14 | 19.1 |
| 0.500 | 146.9 | 8.1 | 2.27 | 14.1 |
| 2.000 | 150.5 | 2.0 | 2.21 | 16.5 |
| Antibiotic LL-E19020β | | | | |
| 0.008 | 161.2 | 0.0 | 2.63 | 0.6 |
| 0.031 | 161.1 | 0.6 | 2.44 | 7.8 |
| 0.125 | 161.6 | 2.0 | 2.19 | 17.4 |
| 0.500 | 156.7 | 3.2 | 2.15 | 18.8 |
| 2.000 | 153.8 | 5.6 | 2.18 | 17.6 |
| AVOPARCIN | | | | |
| 1.0 | 159.4 | 1.8 | 2.38 | 10.2 |
| 2.0 | 160.2 | 0.9 | 2.23 | 15.9 |
| 4.0 | 158.9 | 1.6 | 2.12 | 19.8 |
| 8.0 | 158.3 | 3.2 | 2.08 | 21.3 |
| CONTROL(ACID) | 87.1 | 0.4 | 3.73 | — |

[a] n = 2 unless indicated differently.
[b] n = 6.

TABLE 6

Propionate Enhancement Activity Of Test Compounds During In Vitro Rumen Fermentation

| TREATMENT[a] (PPM) | TOTAL VFA (mM) | (S.D.) | A:P | % DECREASE FROM CONTROL A:P |
|---|---|---|---|---|
| Control[b] | 125.3 | 3.6 | 2.19 | — |
| Antibiotic LL-E19020α | | | | |
| 0.015 | 125.1 | 1.4 | 2.05 | 6.4 |
| 0.031 | 126.5 | 1.5 | 1.96 | 10.7 |
| 0.062 | 126.3 | 2.5 | 1.90 | 13.0 |
| 0.125 | 121.9 | 1.0 | 1.92 | 12.1 |
| 0.250 | 121.1 | 1.2 | 1.85 | 15.5 |
| Antibiotic LL-E19020β | | | | |
| 0.015 | 127.2 | 2.4 | 2.03 | 7.2 |
| 0.031 | 125.7 | 1.1 | 1.98 | 9.5 |
| 0.062 | 123.7 | 0.4 | 1.96 | 10.3 |
| 0.125 | 124.3 | 2.1 | 1.92 | 12.2 |
| 0.250 | 122.6 | 1.5 | 1.93 | 11.9 |
| AVOPARCIN | | | | |
| 1.0 | 126.9 | 1.7 | 2.02 | 7.6 |
| 2.0 | 125.3 | 3.1 | 1.98 | 9.4 |
| 4.0 | 121.3 | 2.0 | 1.90 | 13.1 |
| 8.0 | 119.4 | 0.5 | 1.88 | 14.1 |
| CONTROL(ACID) | 48.7 | 1.1 | 4.41 | — |

[a] n = 3 unless indicated differently.
[b] n = 9.

EXAMPLE 4

Inoculum Preparation

A typical medium used to grow the primary inoculum was prepared according to the following formula:
Dextrose: 1.0%
Dextrin: 2.0%
Yeast extract: 0.5%

NZ Amine A ®[1]: 0.5%
Calcium carbonate: 0.1%
Water qs: 100.0%.

[1] [A pancreatic digest of casein, registered trademark of Sheffield Chemical, Norwich, NY]

This medium was adjusted to pH 7.0 and then sterilized. A 100 ml portion of this sterile medium in a 500 ml flask, was inoculated with mycelial scrapings from an agar slant of *Streptomyces lydicus* ssp. *tanzanius* NRRL 18036. The medium was then placed on a rotary shaker and incubated at 28° C. for 48 hours. This primary inoculum was then used to inoculate 10 liters of the same sterile medium in a bottle. This medium was grown for 24 hours providing secondary inoculum. This secondary inoculum was then used to inoculate 250 liters of the same sterile medium in a tank. This medium was grown at 28° C. for 48 hours with a sterile air flow of 200 liters per liter of mash per minute and agitation by an impeller driven at 220 rpm, providing tertiary inoculum.

EXAMPLE 5

Fermentation

A fermentation medium of the following formulation was prepared:
Dextrin: 3.0%
Molasses: 2.0%
Soy peptone: 0.75%
Yeast extract: 0.25%
Calcium carbonate: 0.2%
Water qs: 100.0%.

This medium was sterilized and 2700 liters was then inoculated with 300 liters of tertiary inoculum from Example 4. The fermentation was conducted at 28° C., with a sterile air flow of 0.55 liters of air per liter of mash per minute and agitation by an impeller driven at 100 rpm for 113 hours, at which time the mash was harvested.

EXAMPLE 6

Isolation and Purification of LL-E19020α and LL-E19020β

The harvest mash from two fermentations conducted as described in Example 5 were combined, making a total of 6000 liters, adjusted to pH 5 with hydrochloric acid and filtered through diatomaceous earth. The filtrate was extracted with ethyl acetate and the extract concentrated to a syrup.

This syrup was dissolved in dichlormethane and applied to 100 g of silica (60–200 mesh) on a sintered glass funnel. The silica column was first eluted with dichloromethane, collecting four 2 liter fractions and then with methanol:dichloromethane (1:4) collecting a 4 liter fraction. This 4 liter fraction was evaporated to dryness, giving 120 g of residue. The residue was redissolved in 4 liters of dichloromethane and applied to 500 g of silica on a sintered glass funnel. The silica was eluted with methanol:dichloromethane (1:4) collecting 2 liter fractions. Fractions 1 and 2 were combined and evaporated, giving 99 g of crude LL-E19020α and β.

This crude product was dissolved in methanol and applied to a 12 liter reverse-phase column (C18 bonded phase 40 micron). The column was eluted with acetonitrile, 0.1M ammonium acetate buffer pH 4.3 (1:1) at a rate of 1.0 liter per minute. Thirteen 24 liter fractions were collected. Fraction 7 contained LL-E19020α and fractions 11-13 contained LL-E19020β.

The antibiotics were extracted from the mobile phase using dichloromethane followed by evaporation and freeze drying from t-butanol, giving 10 g of LL-E19020α and 14 g of LL-E19020β, both as white solids.

What is claimed is:

1. A method of increasing the growth rate of meat producing animals and fish comprising administering to said animals or fish a growth rate increasing amount of antibiotic LL-E19020α comprising
   (a) an elemental analysis: C 62.73; H 7.60; N 1.00; O 28.67 (by difference);
   (b) a molecular weight of 1225 (FABMS);
   (c) a specific optical rotation: $[\alpha]_D^{26} = 0$; (C 0.385, methanol);
   (d) a characteristic ultraviolet absorption spectra as shown in FIG. I of the attached drawings;
   (e) a characteristic infrared absorption spectrum as shown in FIG. II of the attached drawings;
   (f) a characteristic proton nuclear magnetic resonance as shown in FIG. III of the attached drawings; and
   (g) a characteristic carbon-13 nuclear magnetic resonance spectrum as shown in FIG. IV of the attached drawings,
   LL-E19020β comprising
   (a) an elemental analysis: C 63.33; H 7.72; N 1.16; O 27.79 (by difference);
   (b) a molecular weight of 1225 (FABMS);
   (c) a specific optical rotation: $[\alpha]_D^{26} = -17 \pm 2$ (C 0.455, methanol);
   (d) a characteristic ultraviolet absorption spectrum as shown in FIG. V of the attached drawings;
   (e) a characteristic infrared absorption spectrum as shown in FIG. VI of the attached drawings;
   (f) a characteristic proton nuclear magnetic resonance spectrum as shown in FIG. VII of the attached drawings; and
   (g) a characteristic carbon-13 nuclear magnetic resonance spectrum as shown in FIG. VIII of the attached drawings
   or a physiologically-acceptable salt thereof.

2. A method according to claim 1 wherein said antibiotic, or antibiotic salt, is orally administered to said meat producing animals in amounts of from about 0.0001 mg to 50.0 mg/kg body weight per day.

3. A method according to claim 1 wherein said antibiotic, or antibiotic salt, is parenterally administered to meat producing animals in amounts sufficient to provide said animals with from about 0.001 mg to 25 g/head per day of said antibiotic, or antibiotic salt.

4. A method according to claim 1 wherein the meat producing animals are cattle, sheep, swine, goats, horses, poultry or rabbits.

5. A method according to claim 1 wherein said antibiotic, or antibiotic salt is orally administered to fish in an amount sufficient to increase the growth rate of said fish.

6. A method according to claim 2 wherein the meat producing animals are cattle, sheep, swine, goats, horses, poultry or rabbits.

7. A method of increasing the efficiency of feed utilization by meat producing animals comprising orally administering to said meat producing animals a feed efficiency increasing amount of antibiotic LL-E19020α comprising
   (a) an elemental analysis: C 62.73; H 7.60; N 1.00; O 28.67 (by difference);
   (b) a molecular weight of 1225 (FABMS);

(c) a specific optical rotation: $[\alpha]_D^{26} = 0$; (C 0.385, methanol);
(d) a characteristic ultraviolet absorption spectra as shown in FIG. I of the attached drawings;
(e) a characteristic infrared absorption spectrum as shown in FIG. II of the attached drawings;
(f) a characteristic proton nuclear magnetic resonance as shown in FIG. III of the attached drawings; and
(g) a characteristic carbon-13 nuclear magnetic resonance spectrum as shown in FIG. IV of the attached drawings, LL-E19020β comprising
(a) an elemental analysis: C 63.33; H 7.72; N 1.16; O 27.79 (by difference);
(b) a molecular weight of 1225 (FABMS);
(c) a specific optical rotation: $[\alpha]_D^{26} = -17 \pm 2$ (C 0.455, methanol);
(d) a characteristic ultraviolet absorption spectrum as shown in FIG. V of the attached drawings;
(e) a characteristic infrared absorption spectrum as shown in FIG. VI of the attached drawings;
(f) a characteristic proton nuclear magnetic resonance spectrum as shown in FIG. VII of the attached drawings; and
(g) a characteristic carbon-13 nuclear magnetic resonance spectrum as shown in FIG. VIII of the attached drawings
or a physiologically acceptable salt thereof.

8. A method according to claim 7 wherein the animals are ruminant animals having a developed rumen function and the antibiotic is LL-E19020α, LL-E19020β or a physiologically salt thereof and is administered to said ruminant animals in a propionate increasing amount.

9. A method according to claim 8 wherein the ruminants are cattle.

10. A method according to claim 8 wherein the ruminants are sheep.

11. A method according to claim 8 wherein the antibiotic, or antibiotic salt is administered at a rate of from about 0.0001 mg/kg body weight/day to 50.0 mg/kg body weight/day.

12. A method according to claim 7 for increasing the efficiency of feed utilization by poultry by orally administering to said poultry a feed containing from about 0.1 gram to 5 grams per ton of feed of LL-E19020α, LL-E19020β or a physiologically acceptable salt of either antibiotic, per ton of feed.

13. A method for improving lactation in lactating ruminants comprising orally administering to a lactating ruminant having a developed rumen function a lactating increasing amount of antibiotic LL-E19020α comprising
(a) an elemental analysis: C 62.73; H 7.60; N 1.00; O 28.67 (by difference);
(b) a molecular weight of 1225 (FABMS);
(c) a specific optical rotation: $[\alpha]_D^{26} = 0$; (C 0.385, methanol);
(d) a characteristic ultraviolet absorption spectra as shown in FIG. I of the attached drawings;
(e) a characteristic infrared absorption spectrum as shown in FIG. II of the attached drawings;
(f) a characteristic proton nuclear magnetic resonance as shown in FIG. III of the attached drawings; and (g) (h) a characteristic carbon-13 nuclear magnetic resonance spectrum as shown in FIG. IV of the attached drawings, LL-E19020β comprising
(a) an elemental analysis: C 63.33; H 7.72; N 1.16; O 27.79 (by difference);
(b) a molecular weight of 1225 (FABMS);
(c) a specific optical rotation: $[\alpha]_D^{26} = -17 \pm 2$ (C 0.455, methanol);
(d) a characteristic ultraviolet absorption spectrum as shown in FIG. V of the attached drawings;
(e) a characteristic infrared absorption spectrum as shown in FIG. VI of the attached drawings;
(f) a characteristic proton nuclear magnetic resonance spectrum as shown in FIG. VII of the attached drawings; and
(g) a characteristic carbon-13 nuclear magnetic resonance spectrum as shown in FIG. VIII of the attached drawings
or a physiologically acceptable salt thereof.

14. A method according to claim 13 wherein said antibiotic, or antibiotic salt is administered to cattle at from about 0.01 mg/hd/day to 25 g/hd/day.

15. A method according to claim 13 wherein said antibiotic, or antibiotic salt is administered to sheep or goats at from about 0.1 mg/hd/day to 2.5 g/hd/day.

16. An animal feed composition for increasing the growth rate of meat producing animals and fish comprising an edible animal feed and about 0.1 grams to 300 grams of antibiotic LL-E19020α comprising
(a) an elemental analysis: C 62.73; H 7.60; N 1.00; O 28.67 (by difference);
(b) a molecular weight of 1225 (FABMS);
(c) a specific optical rotation: $[\alpha]_D^{26} = 0$; (C 0.385, methanol);
(d) a characteristic ultraviolet absorption spectra as shown in FIG. I of the attached drawings;
(e) a characteristic infrared absorption spectrum as shown in FIG. II of the attached drawings;
(f) a characteristic proton nuclear magnetic resonance as shown in FIG. III of the attached drawings; and
(g) a characteristic carbon-13 nuclear magnetic resonance spectrum as shown in FIG. IV of the attached drawings, LL-E19020β comprising
(a) an elemental analysis: C 63.33; H 7.72; N 1.16; O 27.79 (by difference);
(b) a molecular weight of 1225 (FABMS);
(c) a specific optical rotation: $[\alpha]_D^{26} = -17 \pm 2$ (C 0.455, methanol);
(d) a characteristic ultraviolet absorption spectrum as shown in FIG. V of the attached drawings;
(e) a characteristic infrared absorption spectrum as shown in FIG. VI of the attached drawings;
(f) a characteristic proton nuclear magnetic resonance spectrum as shown in FIG. VII of the attached drawings; and
(g) a characteristic carbon-13 nuclear magnetic resonance spectrum as shown in FIG. VIII of the attached drawings
or a physiologically acceptable salt thereof, per ton of animal feed.

17. An animal feed composition according to claim 16 for cattle, sheep, goats, swine, or horses containing from about 1 gram to 100 grams per ton of feed of antibiotic LL-E19020α, LL-E19020β or a physiologically acceptable salt of either antibiotic.

18. An animal feed composition according to claim 16 for poultry containing from about 1.0 gram to 200 grams per ton of feed of antibiotic LL-E19020α, LL-E19020β or a physiologically acceptable salt thereof.

19. An animal feed composition for increasing the efficiency of food utilization comprising an edible animal feed and an efficiency increasing effective amount of antibiotic LL-E19020α comprising
(a) an elemental analysis: C 62.73; H 7.60; N 1.00; O 28.67 (by difference);
(b) a molecular weight of 1225 (FABMS);
(c) a specific optical rotation: $[alpha]_D^{26} = 0$; (C 0.385, methanol);
(d) a characteristic ultraviolet absorption spectra as shown in FIG. I of the attached drawings; (e) (f) a characteristic infrared absorption spectrum as shown in FIG. II of the attached drawings;
(f) a characteristic proton nuclear magnetic resonance as shown in FIG. III of the attached drawings; and
(g) a characteristic carbon-13 nuclear magnetic resonance spectrum as shown in FIG. IV of the attached drawings,
LL-E19020β comprising
(a) an elemental analysis: C 63.33; H 7.72; N 1.16; O 27.79 (by difference);
(b) a molecular weight of 1225 (FABMS);
(c) a specific optical rotation: $[alpha]_D^{26} = -17 \pm 2$ (C 0.455, methanol); (d) (e) a characteristic ultraviolet absorption spectrum as shown in FIG. V of the attached drawings;
(e) a characteristic infrared absorption spectrum as shown in FIG. VI of the attached drawings;
(f) a characteristic proton nuclear magnetic resonance spectrum as shown in FIG. VII of the attached drawings; and
(g) a characteristic carbon-13 nuclear magnetic resonance spectrum as shown in FIG. VIII of the attached drawings
or a physiologically acceptable salt thereof, per ton of animal feed.

20. An animal feed composition according to claim 19 for cattle, sheep, goats, swine, or horses containing from about 0.1 gram to 300 grams per ton of feed of antibiotic LL-E19020α, LL-E19020β or a physiologically acceptable salt of either antibiotic.

21. An animal feed composition for improving lactation in lactating ruminants comprising an edible animal feed and a lactating effective amount of the antibiotic LL-E19020α comprising
(a) an elemental analysis: C 62.73; H 7.60; N 1.00; O 28.67 (by difference);
(b) a molecular weight of 1225 (FABMS);
(c) a specific optical rotation: $[alpha]_D^{26} = 0$; (C 0.385, methanol);
(d) a characteristic ultraviolet absorption spectra as shown in FIG. I of the attached drawings;
(e) a characteristic infrared absorption spectrum as shown in FIG. II of the attached drawings;
(f) a characteristic proton nuclear magnetic resonance as shown in FIG. III of the attached drawings; and
(g) a characteristic carbon-13 nuclear magnetic resonance spectrum as shown in FIG. IV of the attached drawings,
LL-E19020β comprising
(a) an elemental analysis: C 63.33; H 7.72; N 1.16; O 27.79 (by difference);
(b) a molecular weight of 1225 (FABMS);
(c) a specific optical rotation: $[alpha]_D^{26} = -17 \pm 2$ (C 0.455, methanol);
(d) a characteristic ultraviolet absorption spectrum as shown in FIG. V of the attached drawings;
(e) a characteristic infrared absorption spectrum as shown in FIG. VI of the attached drawings;
(f) a characteristic proton nuclear magnetic resonance spectrum as shown in FIG. VII of the attached drawings; and
(g) a characteristic carbon-13 nuclear magnetic resonance spectrum as shown in FIG. VIII of the attached drawings
or a physiologically acceptable salt thereof, per ton of animal feed.

22. An animal feed composition according to claim 21 for sheep and goats containing from about 0.01 mg/hd/day to 25 g/hd/day of antibiotic LL-E19020α, LL-E19020β or a physiologically acceptable salt of either antibiotic.

* * * * *